(12) United States Patent
Link et al.

(10) Patent No.: US 8,012,212 B2
(45) Date of Patent: Sep. 6, 2011

(54) CERVICAL INTERVERTEBRAL DISK PROSTHESIS

(75) Inventors: Helmut D. Link, Hamburg (DE); Arnold Keller, Kayhude (DE); Paul C. McAfee, Baltimore, MD (US)

(73) Assignee: NuVasive, Inc., San Diego, CA (US)

( * ) Notice: Subject to any disclaimer, the term of this patent is extended or adjusted under 35 U.S.C. 154(b) by 152 days.

(21) Appl. No.: 10/407,946

(22) Filed: Apr. 7, 2003

(65) Prior Publication Data
US 2004/0199253 A1    Oct. 7, 2004

(51) Int. Cl.
*A61F 2/44* (2006.01)
(52) U.S. Cl. .................. 623/17.14; 623/17.15
(58) Field of Classification Search ............. 623/17.11, 623/17.13, 17.15, 17.16, 17.14, 20.19, 20.21, 623/20.34, 20.32; 606/71, 280, 902–906
See application file for complete search history.

(56) References Cited

U.S. PATENT DOCUMENTS

| | | |
|---|---|---|
| 4,911,718 A | 3/1990 | Lee et al. |
| 5,002,576 A * | 3/1991 | Fuhrmann et al. ......... 623/17.15 |
| 5,171,281 A | 12/1992 | Parsons et al. |
| 5,236,460 A | 8/1993 | Barber |
| 5,258,031 A | 11/1993 | Salib et al. |
| 5,290,312 A | 3/1994 | Kojimoto et al. |
| 5,401,269 A * | 3/1995 | Buttner-Janz et al. ..... 623/17.15 |
| 5,425,773 A | 6/1995 | Boyd et al. |
| 5,507,816 A | 4/1996 | Bullivant |
| 5,514,180 A | 5/1996 | Heggeness et al. |
| 5,534,030 A | 7/1996 | Navarro et al. |
| 5,562,738 A | 10/1996 | Boyd et al. |
| 5,645,596 A | 7/1997 | Kim et al. |
| 5,676,701 A | 10/1997 | Yuan et al. |
| 5,888,227 A | 3/1999 | Cottle |
| 5,895,428 A | 4/1999 | Berry |
| 5,989,291 A | 11/1999 | Ralph et al. |
| 6,063,121 A | 5/2000 | Xavier et al. |
| 6,083,228 A | 7/2000 | Michelson |
| 6,113,637 A * | 9/2000 | Gill et al. .................. 623/17.15 |
| 6,156,067 A | 12/2000 | Bryan et al. |
| 6,162,252 A | 12/2000 | Kuras et al. |
| 6,190,410 B1 | 2/2001 | Lamielle et al. |
| 6,228,118 B1 | 5/2001 | Gordon |
| 6,235,059 B1 * | 5/2001 | Benezech et al. .......... 623/17.16 |

(Continued)

FOREIGN PATENT DOCUMENTS

CN    2333369    8/1999

(Continued)

OTHER PUBLICATIONS

Provisional U.S. Appl. No. 60/419,556.*

(Continued)

*Primary Examiner* — Brian E. Pellegrino
(74) *Attorney, Agent, or Firm* — NuVasive, Inc.; Jonathan Spangler; Marjorie Jarvis

(57) ABSTRACT

A cervical intervertebral disk prosthesis has two cover plates, at least one of which is provided with a wedge-shaped connection surface for connection to a vertebral body and which is wider than it is deep. The dorsal edge of the connection surface may be set back from the dorsolateral edge of the cover plate having the connection surface and be connected to the dorsal edge, protruding above it, via a rounding or bevel.

9 Claims, 2 Drawing Sheets

U.S. PATENT DOCUMENTS

| | | | |
|---|---|---|---|
| 6,296,664 B1 | 10/2001 | Middleton | |
| 6,375,682 B1 | 4/2002 | Fleischmann et al. | |
| 6,395,035 B2 | 5/2002 | Bresina et al. | |
| 6,436,140 B1 | 8/2002 | Liu et al. | |
| 6,436,142 B1 | 8/2002 | Paes et al. | |
| 6,443,989 B1 | 9/2002 | Jackson | |
| 6,454,807 B1 | 9/2002 | Jackson | |
| 6,517,580 B1 * | 2/2003 | Ramadan et al. | 623/17.15 |
| 6,572,653 B1 | 6/2003 | Simonson | |
| 6,610,092 B2 | 8/2003 | Ralph et al. | |
| 6,610,093 B1 | 8/2003 | Pisharodi | |
| 6,685,742 B1 | 2/2004 | Jackson | |
| 6,730,126 B2 | 5/2004 | Boehm, Jr. et al. | |
| 6,733,532 B1 | 5/2004 | Gauchet et al. | |
| 6,800,092 B1 | 10/2004 | Williams et al. | |
| 6,805,714 B2 | 10/2004 | Sutcliffe | |
| 6,986,789 B2 | 1/2006 | Schultz et al. | |
| 7,217,291 B2 | 5/2007 | Zucherman et al. | |
| 7,276,082 B2 | 10/2007 | Zdeblick et al. | |
| 7,485,134 B2 | 2/2009 | Simonson | |
| 7,550,010 B2 | 6/2009 | Humphreys et al. | |
| 2001/0008980 A1 | 7/2001 | Gresser et al. | |
| 2001/0016773 A1* | 8/2001 | Serhan et al. | 623/17.15 |
| 2001/0016774 A1 | 8/2001 | Bresina et al. | |
| 2001/0032017 A1 | 10/2001 | Alfaro et al. | |
| 2001/0034553 A1 | 10/2001 | Michelson | |
| 2002/0045943 A1 | 4/2002 | Uk | |
| 2002/0068977 A1 | 6/2002 | Jackson | |
| 2002/0107574 A1 | 8/2002 | Boehm, Jr. et al. | |
| 2002/0128715 A1 | 9/2002 | Bryan et al. | |
| 2002/0128716 A1 | 9/2002 | Cohen et al. | |
| 2002/0143399 A1 | 10/2002 | Sutcliffe | |
| 2002/0169508 A1 | 11/2002 | Songer et al. | |
| 2002/0177898 A1* | 11/2002 | Crozet | 623/17.11 |
| 2002/0193880 A1 | 12/2002 | Fraser | |
| 2003/0069586 A1 | 4/2003 | Errico et al. | |
| 2003/0069643 A1* | 4/2003 | Ralph et al. | 623/17.13 |
| 2003/0125739 A1 | 7/2003 | Bagga et al. | |
| 2003/0130739 A1 | 7/2003 | Gerbec et al. | |
| 2003/0167091 A1 | 9/2003 | Scharf | |
| 2003/0176923 A1 | 9/2003 | Keller et al. | |
| 2003/0181981 A1 | 9/2003 | Lemaire | |
| 2003/0191534 A1 | 10/2003 | Viart et al. | |
| 2003/0204261 A1 | 10/2003 | Eisermann et al. | |
| 2003/0208273 A1 | 11/2003 | Eisermann et al. | |
| 2003/0233146 A1 | 12/2003 | Grinberg et al. | |
| 2004/0010316 A1 | 1/2004 | William et al. | |
| 2004/0068318 A1 | 4/2004 | Coates et al. | |
| 2004/0073310 A1 | 4/2004 | Moumene et al. | |
| 2004/0117021 A1 | 6/2004 | Biedermann et al. | |
| 2004/0133281 A1 | 7/2004 | Khandkar et al. | |
| 2004/0153160 A1 | 8/2004 | Carrasco | |
| 2004/0176850 A1 | 9/2004 | Zubok et al. | |
| 2004/0199253 A1 | 10/2004 | Link et al. | |
| 2004/0254644 A1* | 12/2004 | Taylor | 623/17.15 |
| 2005/0085917 A1 | 4/2005 | Marnay et al. | |
| 2006/0085077 A1 | 4/2006 | Cook et al. | |
| 2006/0116768 A1 | 6/2006 | Krueger et al. | |

FOREIGN PATENT DOCUMENTS

| | | |
|---|---|---|
| DE | 42 13 771 C1 | 9/1993 |
| DE | 4423826 A1 | 1/1995 |
| EP | 0179695 A1 | 4/1986 |
| EP | 0471821 | 2/1992 |
| EP | 0699426 | 3/1996 |
| EP | 0747025 | 12/1996 |
| EP | 0820740 A1 | 1/1998 |
| EP | 1 103 237 A2 | 5/2001 |
| EP | 1166725 A2 | 1/2002 |
| EP | 1344507 A1 | 12/2002 |
| EP | 1344508 A1 | 12/2002 |
| FR | 2 694 882 | 2/1994 |
| FR | 2718635 | 10/1995 |
| FR | 2813519 A1 * | 3/2002 |
| WO | WO 90/00037 | 1/1990 |
| WO | WO 91/13598 A1 | 9/1991 |
| WO | WO 97/20526 A1 | 6/1997 |
| WO | WO 99/08627 A1 | 2/1999 |
| WO | WO 99/65425 A2 | 12/1999 |
| WO | WO-01/01893 | 1/2001 |
| WO | WO-01/54629 A1 | 8/2001 |
| WO | WO 01/91686 | 12/2001 |
| WO | WO 02/11650 A2 | 2/2002 |
| WO | 03/063727 A2 | 8/2003 |
| WO | 03/075803 A1 | 9/2003 |
| WO | 03/075804 A1 | 9/2003 |

OTHER PUBLICATIONS

Link et al., U.S. Office Action mailed Sep. 28, 2009, directed to related U.S. Appl. No. 11/282,604; 8 pages.

Office Action mailed Apr. 4, 2007 in co-pending U.S. Appl. No. 10/552,707.

Office Action mailed Dec. 26, 2007 in co-pending U.S. Appl. No. 10/552,707.

Office Action mailed Jul. 9, 2008 in co-pending U.S. Appl. No. 10/552,707.

Office Action mailed Jan. 22, 2009 in co-pending U.S. Appl. No. 10/552,707.

Office Action mailed Aug. 14, 2009 in co-pending U.S. Appl. No. 10/552,707.

Office Action mailed Mar. 17, 2010 in co-pending U.S. Appl. No. 10/552,707.

International Search Report mailed May 26, 2004 in PCT/EP2004/001029 (corresponding to U.S. Appl. No. 10/552,707).

Office Action mailed Sep. 28, 2009 in co-pending U.S. Appl. No. 11/282,604.

Office Action mailed Aug. 30, 2010 in co-pending U.S. Appl. No. 11/282,604.

* cited by examiner

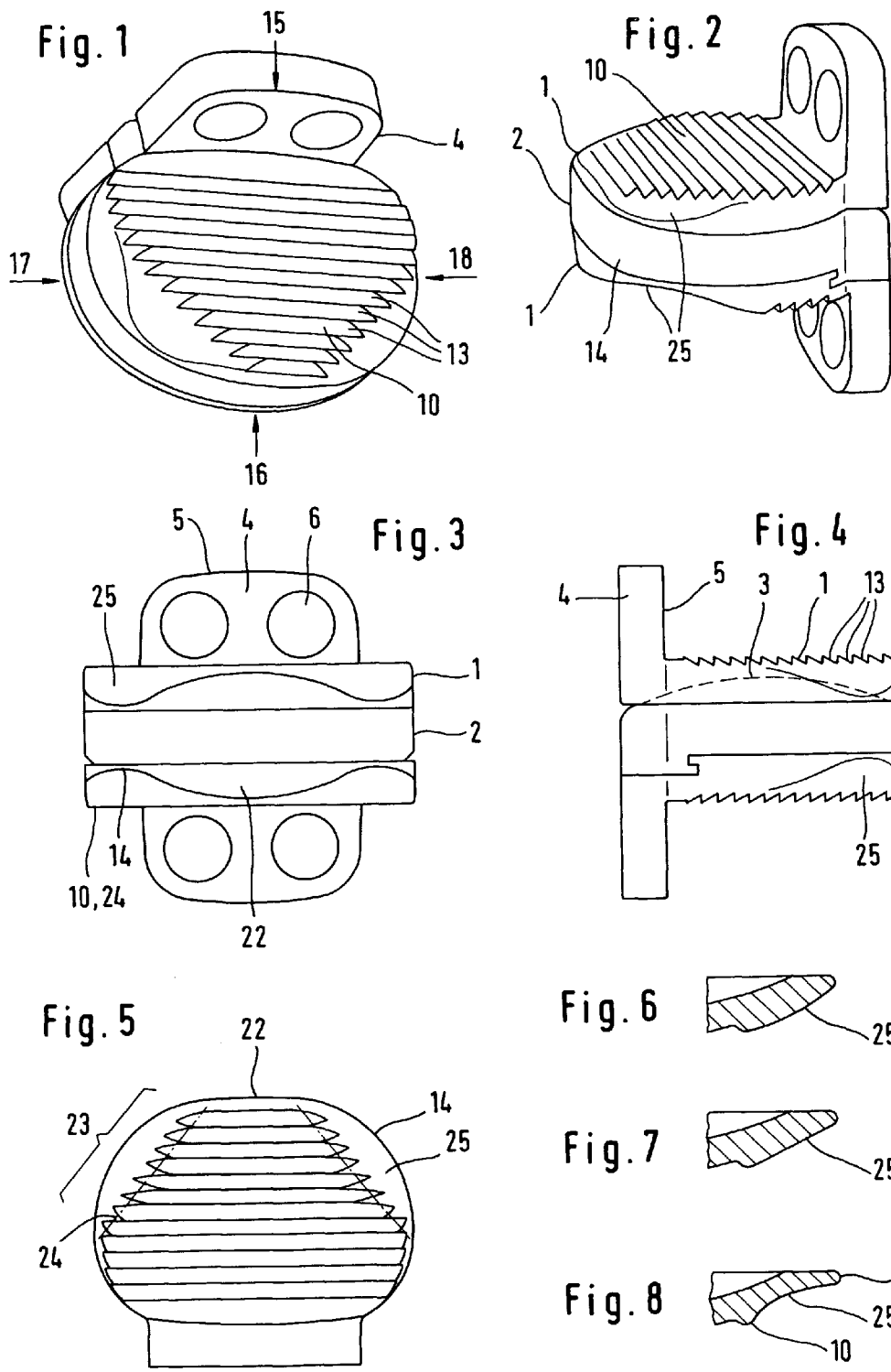

CERVICAL INTERVERTEBRAL DISK PROSTHESIS

BACKGROUND OF THE INVENTION

Endoprostheses for replacement of an intervertebral disk of the cervical spine are known (FR-A-2 718 635, EP-B-699 426) which consist of two cover plates and a joint core. The cover plates, which are arranged approximately parallel on both sides of the core, have connection surfaces which are intended for connection to the adjacent vertebral bodies. The cranial vertebral body cover plates, which are to be connected to a lower prosthesis cover plate, have a roughly rectangular shape. They are approximately flat and are delimited at the sides by edge serrations. The caudal vertebral body cover plates have extensive edge serrations at the ventral edge. These have to be removed before the prosthesis is fitted. It is also expedient for the vertebral body surfaces which are intended to bear on the prosthesis to be worked in order to adapt them to the connection surfaces of the prosthesis.

The connection surfaces of the known prostheses mentioned are circularly delimited. Since the end plates of the vertebral bodies have approximately the shape of a rectangle whose width is substantially greater than its dimension in the anteroposterior direction, they do not exploit the size of the naturally occurring surfaces for force transmission. Accordingly, between the connection surfaces of the prosthesis and the bearing surfaces on the vertebral bodies, greater forces occur than would be the case if the surfaces were better utilized. In the case of intervertebral disk endoprostheses intended for the lumbar spine, the best utilization of space is achieved by using an oval prosthesis contour (WO 0 101 893, EP-B-471 821, EP-A-747 025) or a kidney-shaped configuration (EP-A-747 025), because the cover plates of the vertebral bodies have an oval to kidney-shaped configuration. Rectangular prosthesis shapes are also known (U.S. Pat. No. 5,425,773).

SUMMARY OF THE INVENTION

The object of the invention is to make available an endoprosthesis for replacement of the intervertebral disk in the cervical region of the spine which permits the best possible utilization of space. Since the vertebral body attachment surfaces are approximately rectangular, a similarly approximately rectangular or oval configuration of the connection surfaces of the prosthesis would at first sight seem most appropriate. However, the invention has recognized that better and more reliable results are achieved by using a prosthesis in which at least one of the two connection surfaces, but preferably both connection surfaces, has a configuration in which the connection surface has side edges, a dorsolateral edge and an anteriolateral edge, the side edges inclining toward an imaginary mid-line extending from the ventral edge to the dorsal edge of the cover plate so as to form a wedge shape. The distance from the side edges to their corresponding adjacent dorsal corners of an imaginary rectangle circumscribing a circumferential contour of the cover plate is greater than the distance of the anteriolateral edge from corresponding adjacent ventral corners of the imaginary rectangle.

When shaping the vertebral body bearing surfaces for the prosthesis from the ventral direction, the operating surgeon must keep a safe distance from the spinal canal. This applies in particular when shaping the dorsolateral corners of the bearing surfaces, where visual control is more difficult than in the central dorsal region. This means that in the dorsolateral corners of the vertebral body cover plates bone material may be left which protrudes beyond the worked bearing surface of the vertebral body. If one were to use a rectangular prosthesis, this would not be able to be inserted fully into the intervertebral space because its dorsal corners would strike against the bone material which has been left. If the prosthesis corners are rounded, the circumstances are not much more favorable. The prosthesis then protrudes ventrally beyond the vertebral bodies and may cause irritation of the esophagus or the large blood vessels located there. The set-back, according to the invention, of the prosthesis connection surfaces spares the dorsolateral corners and thereby avoids this disadvantage. By contrast, the surface area of the connection surfaces in their anterolateral regions remains unchanged.

The measure according to the invention can be best described by reference to the distance of the limit of the connection surface from the corner points of an imaginary rectangle which circumscribes the cover plate. It is assumed here that the sides of the rectangle which are tangential to the circumferential contour of the cover plate extend parallel to the sagittal plane or perpendicular thereto. In this context, only those parts intended for accommodation in the intervertebral space are considered as the cover plate. If, for example, a ventral flange is connected to the cover plates and, in the implanted state, lies in front of the ventral end face of the vertebral body, this is not counted as part of the cover plate in the construction of the imaginary rectangle.

The minimum distance of the limit of the connection surface from the dorsal corners of the imaginary rectangle is preferably at least 1.3 times as great, more preferably at least 1.5 times as great, still more preferably at least twice as great as the minimum distance from the ventral corners. It is preferably assumed here that the width of the cover plate is greater than its anteroposterior dimension, generally by a factor of 1.1 to 1.6, preferably by a factor of 1.2 to 1.4.

In general, the connection surfaces of both prosthesis cover plates are configured in accordance with the invention. There are cases, however, where it is sufficient to do this on one of the two connection surfaces, specifically in particular the lower one.

In a particularly preferred embodiment of the invention, the edge of the prosthesis cover plate extends beyond the dorsolateral limit of the associated connection surface. In this way, the cover plate, the prosthesis core and the connection or slide surfaces interacting on the cover plates and the prosthesis core can have an optimum size despite the set-back nature of the connection surface. These parts can therefore be designed, for example, roughly as a rectangular shape with rounded corners.

The transition between the dorsolateral set-back limit of the connection surface to the farther extended edge takes place in the form of an inclined transition surface at both the dorsolateral regions of the cover plate. This can directly adjoin the connection surface. The advantage of this is that the transition surface too can if appropriate participate in the transmission of forces, namely in contact with the bone parts which have been left in the dorsolateral region and protrude beyond the worked bearing surface of the vertebral body. The cross section of the transition surface can be straight, convexly rounded or even stepped.

The term dorsolateral designates the transition region from the lateral aspect to the dorsal aspect of the cover plate. The set-back, according to the invention, of the connection surface is accordingly not restricted only to a dorsal region or a lateral region but instead includes portions of both regions. The term set-back relates to a standard contour of the cover plate which to the front and rear is approximately symmetrical to the middle transverse axis. The limit of the connection surface is set back relative to this standard contour. In case of doubt, the standard contour is the anterolateral contour of the cover plate mirrored about the middle transverse axis. If the cover plate has an edge protruding beyond the limit of the connection surface, which edge does not protrude farther than the standard contour, the set-back of the limit of the connection surface can also be related to the contour of this edge.

Viewed from the lateral direction, the portion in which the limit of the connection surface is set back extends generally over at least one third of the antero-posterior dimension of the connection surface. Viewed from the dorsal direction, this portion generally extends over at least approximately one quarter of the width of the connection surface respectively on both sides. It may be expedient if the connection surface, in a central portion of the dorsal plate edge, is not set back in relation to the latter or is set back less than in the dorsolateral region. This middle portion expediently extends over at least one quarter of the width of the connection surface.

In the ventral third of the lateral sides of the cover plate, the limit of the connection surface is preferably not set back. Slight roundings of the edges of the connection surface are not taken into account here. The set-back of the connection surface limit is preferably at its greatest where it is nearest to the dorsal corner of the imaginary circumscribing rectangle. The set-back limit of the connection surface then has an approximately rectilinear course.

At the place where the difference in height between the set-back limit of the connection surface and the edge protruding above it is at its greatest, the difference in height should be at least approximately 1 mm.

BRIEF DESCRIPTION OF THE DRAWINGS

The invention is explained in greater detail below with reference to the drawing which depicts an advantageous illustrative embodiment, and in which:

FIGS. 1 and 2 show perspective views of the whole prosthesis,

FIG. 3 shows a dorsal side view of the prosthesis,

FIG. 4 shows a lateral view of the prosthesis,

FIG. 5 shows a top view of the outer face of the prosthesis,

FIGS. 6 to 8 show different profiles of the transition surface,

DETAILED DESCRIPTION OF THE INVENTION

Figure 9:
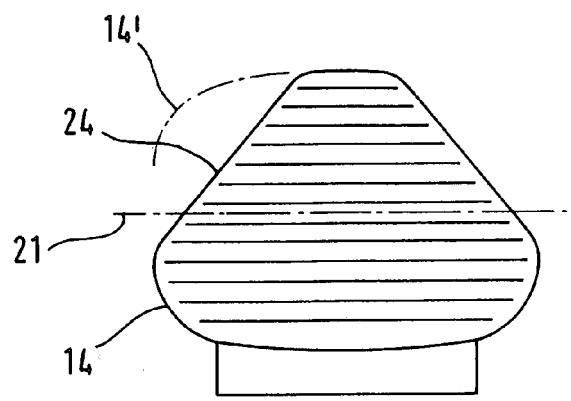
FIG. 9 shows a plan view of an alternative embodiment.

The prosthesis shown in FIGS. 1 to 8 consists of two cover plates 1 and of a prosthesis core 2. The inner face of one of the two cover plates can be provided as a mounting for the prosthesis core 2, while the other cover plate forms, with the prosthesis core, a spherical slide surface 3, for example. At the ventral edge of each cover plate there is a flange 4 whose dorsal face 5 is intended to bear on the ventral face of a vertebral body. The flange can have securing means, for example screw holes 6. Each prosthesis cover plate has a connection surface 10 for bearing on the associated vertebral body cover plate and on the bearing surface created by shaping the vertebral body, said connection surface 10 extending approximately parallel to the main plane of the cover plate. It is substantially flat, but can also have a slight curvature. It is equipped with teeth 13 and/or other means for connecting it securely in position to the bone, for example with a biologically active coating.

Each cover plate is surrounded by a circumferential surface 14 which is approximately perpendicular to the connection surface 10 and which in the present context is designated as an edge. The edge 14 defines the circumferential contour of the cover plate, which has an oblong shape, which can be designated as oval or as rectangular with rounded corners. It is also designated by reference number 14 in FIG. 10. The prosthesis core 2 has the same circumferential contour. The anteroposterior depth dimension 11 of the cover plates 1 is smaller than their width dimension 12, specifically for example in the ratio of three to four. An example which has proven useful has a depth of 15 mm and a width of 20 mm. Its extent is adapted to the vertebral body cover plates and is slightly smaller than these, so that the prosthesis fits into the intervertebral space which is available and has been shaped between the vertebral bodies. If appropriate, it is possible to provide different size categories of prostheses. The cover plates 1 are preferably made of metal, and the core 2 of polyethylene.

Figure 10:
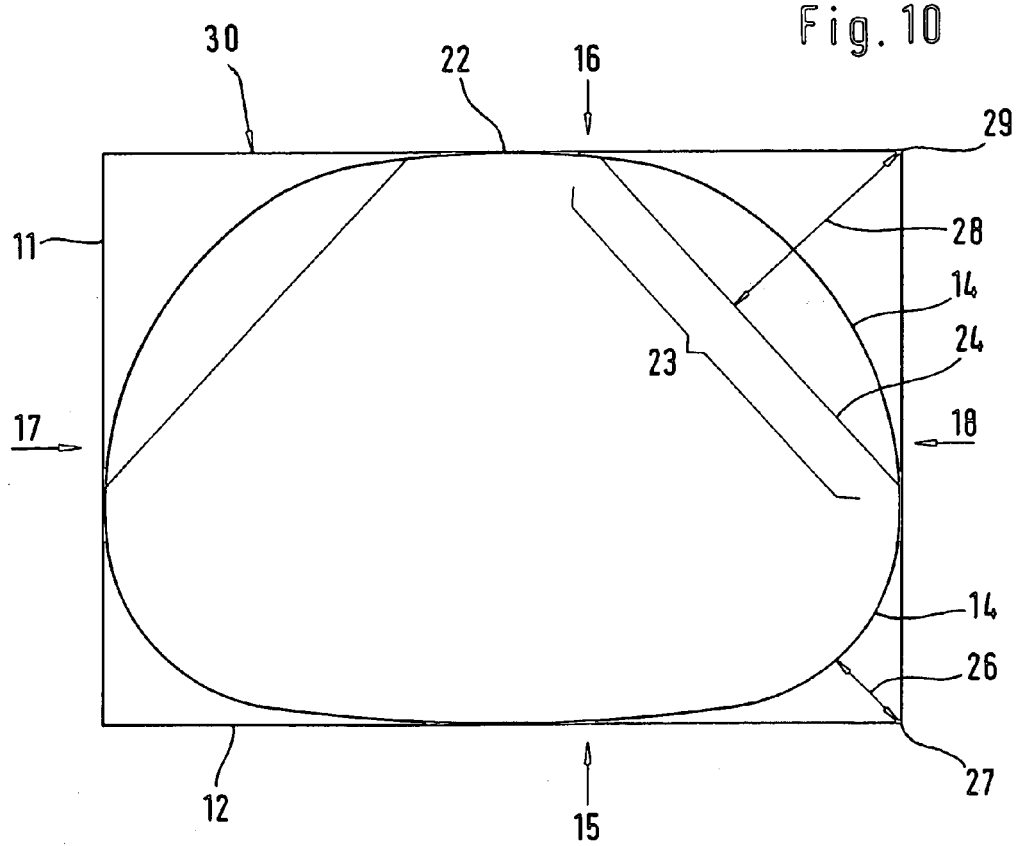
FIG. 10 shows an enlarged representation of the connection surface and the edge contour.

The cover plate 1 or the contour of the edge 14 has a ventral face 15, a dorsal face 16 and lateral faces 17 and 18. Between these there extend the anteroposterior depth dimension 11 and the width dimension 12, which in FIG. 10 are indicated as sides of an imaginary rectangle 21 circumscribing and touching the cover plate or the contour 14 of the edge. Only the part of the cover plate 1 lying behind the flange face 5 is taken into consideration here, since it is only the dimension of the part which will lie in the intervertebral space which is relevant here.

On the ventral face 15 and in the ventral half of the lateral faces 17, 18, the limit of the connection surface 10 follows the contour of the edge 14. They do not need to correspond exactly, because slight deviations in the form of roundings or bevels can be present. The width of these is generally less than 3% of the width dimension 12.

In the transition region from the lateral faces 17, 18 to the dorsal face 16 of the edge, which in the present context is designated as the dorsolateral region, a portion 23 of the limit 24 of the connection surface 10 does not follow the contour 14 but is instead set back relative to the latter. The greatest extent of the set-back, in a plan view, lies between approximately 2 and 5 mm, generally of the order of 2.5 to 3.5 mm. The minimum distance 28 from the corner 29 of the circumscribing rectangle 21 is greater than 13% and preferably greater than 15% and preferably greater than 18% of the width dimension 12. In an illustrative embodiment which has proven useful, it is slightly more than 20% of this width.

The set-back limit 24 relative to the contour 14 is obtained by providing an oblique transition surface 25 between the limit 24 and the edge. Since the transition surface is raised in relation to the plane of the connection surface, a space is obtained below it for receiving the bone parts which have been left in the dorsolateral region upon shaping of the vertebral body surface. It will be appreciated that this space must have an adequate height for this purpose. It should be at least 1 mm at the place of the maximum height difference between the connection surface and the edge 14. The transition surface 25 can, for example, be convexly rounded (FIG. 6) or have a straight profile (FIG. 7). It can also be cut with a step (FIG. 8).

In a side view of the example illustrated, the portion 23 in which the limit 24 is set back relative to the contour 25 of the edge 14 takes up approximately two thirds of the depth dimension 11 and is preferably not less than one third thereof. In the front third, the contour of the cover plate does not deviate from the limit of the connection surface. Slight roundings of the edges are not taken into consideration here.

Viewed from the dorsal direction (FIG. 3), the set-back of the limit 24 of the connection surface decreases toward the center. In a central portion 22 of the dorsal face 16, the edge 14 in practice does not protrude beyond the limit 24. The length of this central portion is preferably between one tenth and one third of the width dimension 12.

The set-back portion 23 of the limit 24 of the connection surface 10 in the dorsolateral region has an approximately rectilinear extent. If one compares it to a rectilinear course connecting the end points of this portion to one another, it scarcely deviates from this course. Any deviation is well below 10% of the length of this course. The end points of said course lie at those points where the deviation of the limit 24 of the connection surface from the circumferential contour 14 goes beyond the extent of the edge roundings otherwise provided.

The deviation of the limit 24 from the circumferential contour 14 in the dorsolateral region is approximately 10% of the cover plate width 12 and should be not less than 5%.

A set-back of the limit of the connection surface in the dorsolateral region—corresponding to the explanations given above—is also shown in the embodiment according to FIG. 9, which differs from that of FIGS. 1 to 8 in that the edge 14 does not extend beyond the limit of the connection surface. The description of the illustrative embodiment in FIGS. 1 to 8 and FIG. 10 correspondingly applies to this illustrative embodiment, except that the course of the limit of the connection surface in the dorsolateral region is not compared to the circumferential contour 14 but instead to the course 14', mirrored about the central transverse axis 21, of the anterolateral circumferential contour 14 of the cover plate.

FIG. 10 illustrates the different course of the limit of the connection surface in the anterolateral region and dorsolateral region, by reference to the corners of the imaginary rectangle 30. It will be noted that the minimum distance 28 of the dorsal corner point 29 from the limit line 24 is almost three times as great as the corresponding minimum distance 26 of the front corner point 27. It should normally be at least 1.5 times as great.

The invention claimed is:

1. An intervertebral prosthesis for replacement of an intervertebral disc, comprising:
   a first cover plate having a first outer face for connection to a first vertebral body and a first inner face forming a first spherical slide surface, the first cover plate having a dorsal edge, ventral edge, and lateral edges defining a perimeter of a circumferential edge, and a connection surface that extends at least partially between the edges of the circumferential perimeter, the connection surface being configured with a series of longitudinal ridges for connection to the first vertebral body;
   a second cover plate having a second outer face for connection to a second vertebral body and a second inner face, the second cover plate having a dorsal edge, ventral edge, and lateral edges defining a perimeter of a circumferential edge and a connection surface that extends at least partially between the edges of the circumferential perimeter, the connection surface being configured with a series of longitudinal ridges for connection to the second vertebral body; and
   a prosthesis core mounted on the inner face of the second cover plate, the prosthesis core forming a spherical slide surface with the inner face of the first cover plate;
   wherein the first cover plate and the second cover plate at their dorsolateral corners are configured with a set-back portion having an inclined transition surface that adjoins a plane of the circumferential edge having a height to a plane of the connection surface having a different height, the set-back portion configured without ridges on the inclined transition surfaces, and providing a space for receiving bone parts which have been left in a dorsolateral region upon shaping of a vertebral body surface.

2. The intervertebral prosthesis of claim 1, wherein the first and second cover plates have a ratio of width to depth of between 1.1:1 and 1.6:1 in a transverse plane.

3. The intervertebral prosthesis of claim 1, wherein the set-back portion has a difference in height of at least 1 mm from the plane of the circumferential edge to the plane of the connection surface of the first and second cover plate.

4. The intervertebral prosthesis of claim 1, wherein the set-back portion extends into a dorsal third of an anteroposterior extent of the connection surface.

5. The intervertebral prosthesis of claim 1, wherein the prosthesis core extends to the edges of the circumferential perimeter of the second cover plate.

6. The intervertebral prosthesis of claim 1, wherein the first and second cover plates are made of metal and the prosthesis core is made of polyethylene.

7. The intervertebral prosthesis of claim 1, wherein the ridges are teeth.

8. The intervertebral prosthesis of claim 1, wherein the first outer face and second outer face is equipped with a biologically active coating.

9. The intervertebral prosthesis of claim 1, wherein the inclined transition surfaces are is at least one of, convexly rounded, straight, and stepped.

* * * * *

UNITED STATES PATENT AND TRADEMARK OFFICE
CERTIFICATE OF CORRECTION

| | |
|---|---|
| PATENT NO. | : 8,012,212 B2 |
| APPLICATION NO. | : 10/407946 |
| DATED | : September 6, 2011 |
| INVENTOR(S) | : Helmut D. Link et al. |

It is certified that error appears in the above-identified patent and that said Letters Patent is hereby corrected as shown below:

On the Title page of the patent, Assignee name, please delete "NuVasive, Inc." and replace with --Cervitech, Inc.--

Signed and Sealed this
Fourth Day of October, 2011

David J. Kappos
*Director of the United States Patent and Trademark Office*